US011105027B2

(12) United States Patent
Hartgrove et al.

(10) Patent No.: US 11,105,027 B2
(45) Date of Patent: Aug. 31, 2021

(54) CLEANING FABRIC

(71) Applicant: Berry Global, Inc., Evansville, IN (US)

(72) Inventors: Herbert P. Hartgrove, Dunn, NC (US); Sayanti Basu, Charlotte, NC (US); Jerry Snider, Mooresville, NC (US)

(73) Assignee: Berry Global, Inc., Evansville, IN (US)

( * ) Notice: Subject to any disclaimer, the term of this patent is extended or adjusted under 35 U.S.C. 154(b) by 208 days.

(21) Appl. No.: 16/153,160

(22) Filed: Oct. 5, 2018

(65) Prior Publication Data
US 2019/0106819 A1   Apr. 11, 2019

Related U.S. Application Data

(60) Provisional application No. 62/568,937, filed on Oct. 6, 2017.

(51) Int. Cl.
*D04H 1/492* (2012.01)
*D04H 1/488* (2012.01)
(Continued)

(52) U.S. Cl.
CPC .............. *D04H 1/492* (2013.01); *A47L 13/16* (2013.01); *B08B 1/006* (2013.01);
(Continued)

(58) Field of Classification Search
CPC .... D04H 1/492; D04H 1/43835; D04H 1/587; D04H 1/43912; D04H 1/43838;
(Continued)

(56) References Cited

U.S. PATENT DOCUMENTS 4,101,520 A * 7/1978 Boldizar ................ C08G 12/32
524/512
4,610,920 A * 9/1986 Mudge ................ D06M 15/227
427/391

(Continued)

FOREIGN PATENT DOCUMENTS

EP   1696063 A1   8/2006
EP   2431512 A1   3/2012
(Continued)

OTHER PUBLICATIONS

"JP2010259633_Machine Translation" is a machine translation of JP-2010259633-A. (Year: 2010).*
(Continued)

*Primary Examiner* — Marla D McConnell
*Assistant Examiner* — Larissa Rowe Emrich
(74) *Attorney, Agent, or Firm* — Burr & Forman LLP

(57) ABSTRACT

Fabrics are provided that include mono-component staple fibers, a first group of split staple fibers comprising a first polymeric material, and a second group of split staple fibers comprising a second polymeric material that is different than the first polymeric material. The mono-component staple fibers, the first group of split staple fibers, and the second group of split staple fibers are physically entangled together to define a consolidated nonwoven. The fabrics may be physically entangled by hydroentanglement.

10 Claims, 3 Drawing Sheets

(51) Int. Cl.
| | |
|---|---|
| *D04H 1/4391* | (2012.01) |
| *D04H 1/4382* | (2012.01) |
| *D04H 1/587* | (2012.01) |
| *A47L 13/16* | (2006.01) |
| *D04H 1/74* | (2006.01) |
| *B08B 1/00* | (2006.01) |
| *A61L 2/18* | (2006.01) |

(52) U.S. Cl.
CPC ..... *D04H 1/43825* (2020.05); *D04H 1/43835* (2020.05); *D04H 1/43838* (2020.05); *D04H 1/43912* (2020.05); *D04H 1/488* (2013.01); *D04H 1/587* (2013.01); *D04H 1/74* (2013.01); *A61L 2/18* (2013.01); *D10B 2321/02* (2013.01); *D10B 2331/04* (2013.01)

(58) Field of Classification Search
CPC ...... D04H 1/43825; D04H 1/488; D04H 1/74; D04H 1/4391; D04H 1/49; B08B 1/006; A61L 2/18; C09J 109/02; C09J 131/04; C09J 131/08; C09J 131/12; C09J 131/20; C09J 131/26; C09J 161/28
See application file for complete search history.

(56) References Cited

U.S. PATENT DOCUMENTS

| | | | | |
|---|---|---|---|---|
| 5,759,926 | A * | 6/1998 | Pike | D04H 1/4382 442/333 |
| 5,935,883 | A * | 8/1999 | Pike | D01D 5/0985 442/340 |
| 6,034,005 | A * | 3/2000 | Diehl | C08F 236/10 442/104 |
| 2002/0006502 | A1 * | 1/2002 | Nagaoka | D04H 1/4334 428/198 |
| 2002/0037408 | A1 * | 3/2002 | Tsutsui | D04H 1/4382 428/373 |
| 2003/0176132 | A1 * | 9/2003 | Moriyasu | D04H 1/4382 442/361 |
| 2005/0287895 | A1 * | 12/2005 | Bansal | D04H 3/018 442/361 |
| 2006/0009106 | A1 * | 1/2006 | Nishimura | D04H 1/54 442/404 |
| 2006/0205310 | A1 * | 9/2006 | Schubert | D04H 1/492 442/361 |
| 2007/0178795 | A1 * | 8/2007 | Stralin | D04H 1/4382 442/408 |
| 2012/0066852 | A1 * | 3/2012 | Trinkaus | D04H 1/492 15/104.93 |
| 2016/0249606 | A1 | 9/2016 | Hartgrove et al. | |
| 2016/0250668 | A1 | 9/2016 | Hartgrove et al. | |

FOREIGN PATENT DOCUMENTS

| | | | |
|---|---|---|---|
| JP | H06101148 | A | 4/1994 |
| JP | 2004330007 | A | 11/2004 |
| JP | 2010259633 | A * | 1/2010 |
| JP | 2010259633 | A | 11/2010 |
| WO | 2006001739 | A1 | 1/2006 |
| WO | 2016138228 | A1 | 9/2016 |
| WO | 2017001457 | A1 | 1/2017 |

OTHER PUBLICATIONS

International Search Report and Written Opinion of PCT/US2018/054675 dated Feb. 11, 2019, all enclosed pages cited.

International Preliminary Report on Patentability issued in corresponding international application No. PCT/US2018/054675 dated Nov. 6, 2019, all enclosed pages cited.

* cited by examiner

CLEANING FABRIC

PRIORITY CLAIM

This application claims priority under 35 U.S.C. § 119(e) to U.S. Provisional Application Ser. No. 62/568,937 filed Oct. 6, 2017, which is expressly incorporated by reference herein in its entirety.

TECHNICAL FIELD

Embodiments of the presently-disclosed invention relate generally to fabrics suitable as a cleaning fabric (e.g., a nonwoven wipe) that provides one or more of adequate dwell time, abrasion resistance, and compatibility with a variety of disinfectants, such as quaternary ammonium compounds and chlorine-based disinfectants.

BACKGROUND

Commercial disinfectant wipes commonly employ quaternary ammonium ("Quat") disinfectants or chlorine-based disinfectants. Quat-based disinfectants are effective disinfectants because they carry a positive charge, while bacteria, viruses, fungi and/or the like carry a negative charge. When a Quat-based disinfectant solution is applied to a surface, the charge of the bacterial cell changes from negative to positive and disrupts the bacterial cell wall, which eventually causes cell death. Some wipes incorporate the Quat solution (e.g., wet-wipe), while others allow consumers to use their own Quat disinfectant in conjunction with the wipes so that they may vary the Quat concentration used. Chlorine disinfectants are popular disinfectants because they are relatively inexpensive and fast-acting. Furthermore, chlorine disinfectants are particularly effective against biofilms and biological membranes.

Regardless, some wipes have been found to deplete Quat or chlorine-based compounds in a solution over time due to ionic chemical reactions between the fabric (e.g., wipe) and the Quat or the chlorine-based compounds. This depletion is a concern for food service (e.g., restaurant operators) and/or food industry operators because they want the disinfecting solution to contain the right concentration of the disinfectant chemicals. This desire, at least in part, is driven by the fear of fines in the event that a government inspector finds the solution in the container to be under a minimum level. The operators typically select a concentration level above that minimum level without greatly exceeding it because of the cost and the potentially negative impact on consumer safety and perception if great excess of disinfectant is left on the surface being disinfected. Therefore, the operators desire a wipe that does not deplete the concentration of the disinfecting solution.

While wipes treated with a specific chemistry are available that do not deplete considerably either the concentration of a Quat or the concentration of a chlorine-based compound; it is desirable for them to have a wipe that can be used with either type of disinfectant without depletion of the disinfectant. Some wipes attempt to provide this feature, but undesirably release too much of the sanitizing solution when first put in contact with the surface to be sanitized. Such wipes, therefore, provide an excessive dwell time for the solution, in which dwell time is the time needed for the film of solution to evaporate from the treated surface.

Dwell time is important to, for example, food service establishment operators as it may impair their ability to service customer rapidly. To be properly disinfected, the surface of a table, for example, must stay wet with the disinfecting solution for a minimum of 60 seconds in order to kill the microbes. The restaurant operators want to consistently exceed that minimum dwell time for the disinfecting solution and be able to clean a good area between occurrences of needing to replenish the solution in the wipe. When a wipe delivers an excessive amount of disinfecting solution on first contact, the surface of the first table wiped will take a longer time to dry up (e.g., well in excess of the 60 seconds needed). This excess time to dry may cause delays and prevent the table to be used by customers for longer than desirable. Also, if the wipe delivers too much disinfecting solution when first applied to the surface, the solution contained in the wipe will be depleted rapidly and it will impair its ability to cover a large surface area before having to be replenished with solution.

Therefore, there remains a need in the art for a fabric (e.g., wipe) that provides one or more of the following: compatibility (e.g., mitigates depletion of a disinfectant concentration) with a variety of disinfectants, such as quaternary ammonium compounds and chlorine-based disinfectants; provide a desirable dwell time (e.g., desired or controlled release of the disinfecting solution); abrasion resistance; and not stain easily (e.g., not retain color of soiling material even after is it rinsed or washed).

SUMMARY OF INVENTION

One or more embodiments of the invention may address one or more of the aforementioned problems. Certain embodiments according to the invention provide a fabric (e.g., a nonwoven wipe) including mono-component staple fibers comprising from about 1 to about 4 decitex (dtex), a first group of split staple fibers comprising from about 0.05 to about 0.5 dtex, and a second group of split staple fibers comprising from about 0.05 to about 0.5 dtex. In this regard, the first group of split staple fibers and the second group of split staple fibers may be present due to the complete or partial splitting or separation of individual segments from splittable multi-component staple fibers, in which the "split fiber" may comprise the portion of an individual segment of the splittable multi-component staple fiber that has been separated or split from the original splittable multi-component staple fiber. In accordance with certain embodiments of the invention, the first group of split staple fibers may comprise a first polymeric material and the second group of split staple fibers may comprise a second polymeric material that is different than the first polymeric material. In accordance with certain embodiments of the invention, the mono-component staple fibers, the first group of split staple fibers, and the second group of split staple fibers are physically entangled together to define a consolidated nonwoven. In accordance with certain embodiments of the invention, the fabric comprises a hydroentangled nonwoven. The fabric, in accordance with certain embodiments of the invention, may be devoid of any synthetic and/or cellulosic material.

In another aspect, the present invention provides a fabric comprising a blend of physically entangled fibers. In accordance with certain embodiments of the invention, the blend of fibers may comprise mono-component staple fibers comprising from about 1 to about 4 decitex (dtex) and splittable multi-component staple fibers comprising from about 1 to about 4 dtex, in which the splittable multi-component staple fibers include at least about 6 splittable segments and the splittable multi-component staple fibers comprise from about 15 to about 50% by weight of the blend of fibers. In accordance with certain embodiments of the invention, the mono-component staple fibers and splittable multi-component staple fibers define a carded web, which may optionally be devoid of synthetic and/or natural cellulosic material.

In another aspect, the present invention provides a method for forming a fabric, such as a fabric disclosed herein. In accordance with certain embodiments of the invention, the method comprises providing a blend of fibers, in which the blend of fibers comprises (a) mono-component staple fibers comprising from about 1 to about 4 decitex (dtex) and (b) splittable multi-component staple fibers comprising from about 1 to about 4 dtex. The splittable multi-component staple fibers, for example, may include at least about 6 splittable segments and the splittable multi-component staple fibers may comprise from about 15 to about 50% by weight of the blend of fibers. The method may further comprise physically entangling the blend of fibers to at least partially split the splittable multi-component staple fibers and to provide a consolidated nonwoven. In accordance with certain embodiments of the invention, the step of physically entangling the blend of fibers comprises hydroentangling the blend of fibers.

In yet another aspect, the present invention provides a method of treating a surface (e.g., disinfecting a surface). In accordance with certain embodiments of the invention, the method may comprise a step of providing a fabric (e.g., a wipe) according to a fabric disclosed herein and applying a liquid disinfectant composition to the fabric. The method may further comprise contacting the surface with the fabric to transfer at least a portion of the liquid disinfectant onto the surface. In accordance with certain embodiments of the invention, the step of applying a liquid disinfectant composition to the fabric comprises submerging the fabric into a container holding the liquid disinfectant.

BRIEF DESCRIPTION OF THE DRAWING(S)

The invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout, and wherein.

DETAILED DESCRIPTION

Figure 1A:
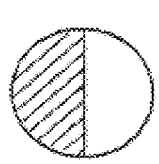
FIGS. 1A-1H illustrates examples of cross-sections for some splittable multi-component fibers in accordance with certain embodiments of the invention.
Figure 1B:
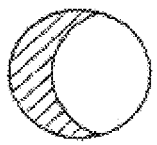
Figure 1C:
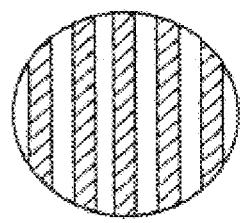
Figure 1D:
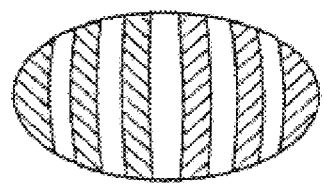
Figure 1E:
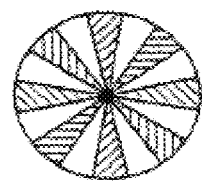
Figure 1F:
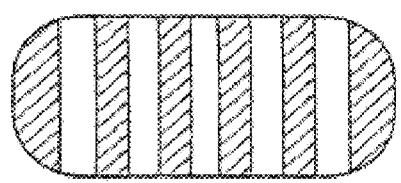
Figure 1G:
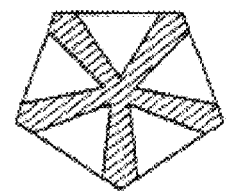
Figure 1H:
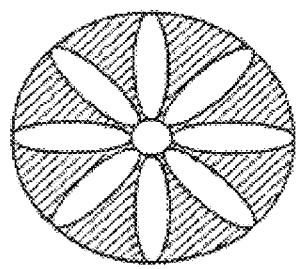

The invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The presently-disclosed invention relates generally to fabrics suitable as a cleaning fabric (e.g., a nonwoven wipe) that provides one or more of adequate dwell time, abrasion resistance, and compatibility with a variety of disinfectants, such as quaternary ammonium compounds and chlorine-based disinfectants. In accordance with certain embodiment of the invention, the fabrics comprise or consist of a hydroentangled nonwoven suitable for use with a sanitizer/disinfectant. For example, the hydroentangled nonwoven may be a substantially dry fabric that can be used with a variety of disinfectant solutions at or near a point and/or time of use. In this regard, a single hydroentangled nonwoven, in accordance with certain embodiments of the invention, may be used with more than one type of disinfectant (e.g., quaternary ammonium compounds and chlorine-based disinfectants) over the course of a lifetime of use. In accordance with certain embodiments of the invention, the fabrics may be devoid of cellulosic materials (e.g., natural and/or synthetic cellulosic fibers). For example, all fibers forming the fabric may be made of one or more synthetic polymers. In accordance with certain embodiments of the invention, all or substantially all of the ingredients/components (e.g., fibers, binders, additives, etc.) may be selected and/or configured for exhibiting no or low reactivity with the sanitizing/disinfecting chemicals. The flow or release of a disinfecting solution that has been loaded onto the fabric may be controlled, in accordance with certain embodiments of the invention, through tuning of the pore size distribution by using fibers of different diameters. For instance, the pore size distribution may be modified by introduction of splittable fibers (e.g., in split, partially split, or yet to be split form) to provide microfibers dispersed between the larger or more coarse fibers, such as larger decitex staple fibers. Spittable fibers or split fibers derived from splittable fibers may comprise a variety of synthetic polymer combinations, such as polyethylene terephthalate (PET)/polypropylene (PP) splittable multi-component fibers and/or PET/polyamide (PA) splittable multi-component fibers to produce the microfibers. In accordance with certain embodiments of the invention, the use of PP/PET splittable multi-component fibers may provide an improved stain resistance and further enhance the non-reactivity with the disinfectant. For instance, nylons have more affinity than polypropylene to bind with the molecules responsible for staining. In accordance with certain embodiments of the invention, the fabrics (e.g., hydroentangled nonwoven) may comprise an acrylic binder (e.g., non-ionic acrylic binder) alone or in addition to other binder components to optionally improve the abrasion resistance. In accordance with certain embodiments of the invention, the use of an acrylic binder (e.g., non-ionic acrylic binder) may considerably reduce the loss of fiber by abrasion while not being significantly reactive with the disinfectant.

In accordance with certain embodiments of the invention, the introduction of splittable fibers (e.g., in split, partially split, or yet to be split form) that produce microfibers (e.g., split fibers) may account for about 10 to about 50% of the weight of total fibers of the fabric and create a network of finer pore or capillaries between the larger fibers (e.g., mono-component staple fibers) that holds or retains a liquid disinfectant solution better (e.g., longer residence time for a given wiping pressure). In this regard, split staple fibers may be present due to the complete or partial splitting or separation of individual segments from splittable multi-component staple fibers, in which the "split fiber" may comprise the portion of an individual segment of the splittable multi-component staple fiber that has been separated or split from the original splittable multi-component staple fiber. In this regard, certain embodiments of the invention, may comprise a combination of mono-component staple fibers, one of more groups of split staple fibers, and/or spittable multi-component staple fibers. By increasing the retention ability of a liquid disinfectant loaded onto the fabric, the disinfectant solution may be released more progressively under the pressure exercised on the fabric during the act of wiping a hard surface. In accordance with certain embodiments of the invention, the use of splittable fibers and/or split fibers in the fabric for the application of depositing a disinfectant solution to a surface provides several benefits.

The terms "substantial" or "substantially" may encompass the whole amount as specified, according to certain embodiments of the invention, or largely but not the whole amount specified (e.g., 95%, 96%, 97%, 98%, or 99% of the whole amount specified) according to other embodiments of the invention.

The terms "polymer" or "polymeric", as used interchangeably herein, may comprise homopolymers, copolymers, such as, for example, block, graft, random, and alternating copolymers, terpolymers, etc., and blends and modifications thereof. Furthermore, unless otherwise specifically limited, the term "polymer" or "polymeric" shall include all possible structural isomers; stereoisomers including, without limitation, geometric isomers, optical isomers or enantionmers; and/or any chiral molecular configuration of such polymer or polymeric material. These configurations include, but are not limited to, isotactic, syndiotactic, and atactic configurations of such polymer or polymeric material. The term "polymer" or "polymeric" shall also include polymers made from various catalyst systems including, without limitation, the Ziegler-Natta catalyst system and the metallocene/single-site catalyst system. The term "polymer" or "polymeric" shall also include, in according to certain embodiments of the invention, polymers produced by fermentation process or biosourced.

The terms "nonwoven" and "nonwoven web", as used herein, may comprise a web having a structure of individual fibers, filaments, and/or threads that are interlaid but not in an identifiable repeating manner as in a knitted or woven fabric. Nonwoven fabrics or webs, according to certain embodiments of the invention, may be formed by any process conventionally known in the art such as, for example, meltblowing processes, spunbonding processes, needle-punching, hydroentangling, air-laid, and bonded carded web processes.

The term "staple fiber", as used herein, may comprise a cut fiber from a filament. In accordance with certain embodiments, any type of filament material may be used to form staple fibers. For example, staple fibers may be formed from polymeric fibers, and/or elastomeric fibers. Non-limiting examples of materials may comprise polyolefins (e.g., a polypropylene or polypropylene-containing copolymer), polyethylene terephthalate, and polyamides. The average length of staple fibers may comprise, by way of example only, from about 2 centimeter to about 15 centimeter.

The term "layer", as used herein, may comprise a generally recognizable combination of similar material types and/or functions existing in the X-Y plane.

The term "multi-component fibers", as used herein, may comprise fibers formed from at least two different polymeric materials (e.g., two or more) extruded from separate extruders but spun together to form one fiber. The term "bi-component fibers", as used herein, may comprise fibers formed from two different polymeric materials extruded from separate extruders but spun together to form one fiber.

The polymeric materials or polymers are arranged in a substantially constant position in distinct zones across the cross-section of the multi-component fibers and extend continuously along the length of the multi-component fibers. The configuration of such a multi-component fibers may be, for example, a sheath/core arrangement wherein one polymer is surrounded by another, or may be a side-by-side arrangement, a pie arrangement, or an "islands-in-the-sea" arrangement, each as is known in the art of multicomponent, including bicomponent, fibers.

The term "hydroentangle" or "hydroentangled", as used herein, may comprise a nonwoven fabric or process for bonding a nonwoven fabric by using high pressure water jets to intermingle the fibers. Several rows of water jets are directed against the fiber web, which is supported by a movable fabric. Fiber entanglements are introduced by the combined effects of the water jets and the turbulent water created in the web, which intertwines neighboring fibers.

All whole number end points disclosed herein that can create a smaller range within a given range disclosed herein are within the scope of certain embodiments of the invention. By way of example, a disclosure of from about 10 to about 15 includes the disclosure of intermediate ranges, for example, of: from about 10 to about 11; from about 10 to about 12; from about 13 to about 15; from about 14 to about 15; etc. Moreover, all single decimal (e.g., numbers reported to the nearest tenth) end points that can create a smaller range within a given range disclosed herein are within the scope of certain embodiments of the invention. By way of example, a disclosure of from about 1.5 to about 2.0 includes the disclosure of intermediate ranges, for example, of: from about 1.5 to about 1.6; from about 1.5 to about 1.7; from about 1.7 to about 1.8; etc.

In one aspect, the invention provides a fabric (e.g., a nonwoven wipe) including mono-component staple fibers comprising from about 1 to about 4 decitex (dtex), a first group of split staple fibers comprising from about 0.05 to about 0.5 dtex, and a second group of split staple fibers comprising from about 0.05 to about 0.5 dtex. In this regard, the first group of split staple fibers and the second group of split staple fibers may be present due to the complete or partial splitting or separation of individual segments from splittable multi-component staple fibers, in which the "split fiber" may comprise the portion of an individual segment of the splittable multi-component staple fiber that has been separated or split from the original splittable multi-component staple fiber. In accordance with certain embodiments of the invention, the first group of split staple fibers may comprise a first polymeric material and the second group of split staple fibers may comprise a second polymeric material that is different than the first polymeric material. In accordance with certain embodiments of the invention, the mono-component staple fibers, the first group of split staple fibers, and the second group of split staple fibers are physically entangled together to define a consolidated nonwoven. In accordance with certain embodiments of the invention, the fabric comprises a hydroentangled nonwoven. The fabric, in accordance with certain embodiments of the invention, may be devoid of any synthetic and/or cellulosic material.

In accordance with certain embodiments of the invention, the consolidated nonwoven comprises a hydroentangled nonwoven. In accordance with certain embodiments of the invention, the hydroentangled nonwoven may be formed by positioning a first surface of the fabric directly or indirectly onto an image transfer device having a three-dimensional pattern and applying jets of fluid directly or indirectly to a second surface of the fabric to impart a three-dimensional pattern onto the hydroentangled nonwoven fabric. For example, according to certain embodiments of the invention, the image transfer device may comprise one or more drums or even one or more sleeves affixed to a corresponding drum. One or more water jets, for example, high pressure water jets according to certain embodiments of the invention, may be applied to a side of the nonwoven opposite to the side contacting the image transfer device. Without intending to be bound by the theory, the one or more water jets and water directed through the nonwoven causes the fibers of the nonwoven to become displaced according to the image on the image transfer device such as the image formed on one or more drums or one or more sleeves affixed to a corresponding drum causing a three-dimensional pattern to be imaged throughout the nonwoven according to such image.

The fabric, in accordance with certain embodiments of the invention, may comprises a basis weight from about 20-200 grams-per-square-meter (gsm), such as from about 25-150 gsm, 30-140 gsm, 30-90 gsm, 40-80 gsm, 50-70 gsm, 55-70 gsm, or from about 60-70 gsm. For instance, the fabric may comprise a basis weight of at most about any of the following: 200, 190, 180, 170, 160, 150, 140, 135, 130, 125, 120, 115, 110, 105, 100, 90, 80, 70, 65, 60, and 55 gsm and/or at least about any of the following: 20, 30, 40, 50, 55, 60, 65, 70, 75, 80, 85, 90, 95, 100, 105, 110, 115, and 120 gsm.

The fabric, in accordance with certain embodiments of the invention, may comprise a pore size distribution comprising a plurality of fine pores and/or capillaries formed between larger (e.g., course) mono-component staple fibers and smaller (e.g., fine) split staple fibers formed from the splitting of splittable multi-component staple fibers. The pore size distribution, for example, having a plurality of fine pores and/or capillaries may control the flow or release of a disinfecting solution that has been loaded onto the fabric. For example, the use of fibers having differing diameters or decitex may provide a pore size distribution that holds or retains a liquid disinfectant solution better (e.g., longer residence time for a given wiping pressure). In this regard, split staple fibers may be present due to the complete or partial splitting or separation of individual segments from splittable multi-component staple fibers, in which the "split fiber" may comprise the portion of an individual segment of the splittable multi-component staple fiber that has been separated or split from the original splittable multi-component staple fiber. In this regard, certain embodiments of the invention, may comprise a combination of mono-component staple fibers, one of more groups of split staple fibers, and/or spittable multi-component staple fibers. By increasing the retention ability of a liquid disinfectant loaded onto the fabric, the disinfectant solution may be released more progressively under the pressure exercised on the fabric during the act of wiping a hard surface. In accordance with certain embodiments of the invention, the use of splittable fibers and/or split fibers in the fabric for the application of depositing a disinfectant solution to a surface provides several benefits.

In accordance with certain embodiments of the invention, the mono-component staple fibers may have a linear mass density of at most about 5 decitex (dtex), such as at most about 4, 3, 2.5, 2, or 1.5 dtex. In accordance with certain embodiments of the invention, for example, the mono-component staple fibers may have a linear mass density of at most about any of the following: 6, 5.5, 5, 4.5, 4, 3.5, 3, 2.5, 2, and 1.5 dtex and/or at least about any of the following: 1, 1.25, 1.5, 1.75, and 2.0 dtex.

In accordance with certain embodiments of the invention, the first group of split stable fibers and the second group of split stable fibers may independently have a linear mass density of at most about 1 decitex (dtex), such as at most about 0.75, 0.5, 0.25, 0.2, 0.1, 0.75, or 0.5 dtex. In accordance with certain embodiments of the invention, for example, the first group of split stable fibers and the second group of split stable fibers may independently comprise at most about any of the following: 1, 0.75, 0.5, 0.25, 0.2, 0.1, 0.75, 0.5, and 0.25 dtex and/or at least about any of the following: 0.05, 0.075, 0.1, 0.125, 0.15, 0.2, and 0.25 dtex.

In accordance with certain embodiments of the invention, the splittable multi-component staple fibers may have a linear mass density of at most about 5 decitex (dtex), such as at most about 4, 3, 2.5, 2, or 1.5 dtex. In accordance with certain embodiments of the invention, for example, the splittable multi-component staple fibers may have a linear mass density of at most about any of the following: 6, 5.5, 5, 4.5, 4, 3.5, 3, 2.5, 2, and 1.5 dtex and/or at least about any of the following: 1, 1.25, 1.5, 1.75, and 2.0 dtex.

In accordance with certain embodiments of the invention, the total amount of split staple fibers comprises from about 10% to 50% by weight of a total amount of fibers forming the fabric, in which the total amount of split staple fibers may be defined by the sum of the first group of split staple fibers and the second group of split staple fibers. In accordance with certain embodiments of the invention, for instance, the total amount of split staple fibers comprises may comprise at most about any of the following: 75%, 65%, 55%, 50%, 45%, 40%, 35%, and 30% by weight of a total amount of fibers forming the fabric and/or at least about any of the following: 10%, 15%, 20%, 25%, 30%, and 35% by weight of a total amount of fibers forming the fabric.

In accordance with certain embodiments of the invention, the total amount of splittable multi-component staple fibers comprises from about 10% to 50% by weight of a total amount of fibers forming the fabric. In accordance with certain embodiments of the invention, for instance, the total amount of splittable multi-component staple fibers may comprise at most about any of the following: 75%, 65%, 55%, 50%, 45%, 40%, 35%, and 30% by weight of a total amount of fibers forming the fabric and/or at least about any of the following: 10%, 15%, 20%, 25%, 30%, and 35% by weight of a total amount of fibers forming the fabric.

In accordance with certain embodiments of the invention, the sum of splittable multi-component staple fibers and split staple fibers may comprises from about 10% to 50% by weight of a total amount of fibers forming the fabric. In accordance with certain embodiments of the invention, for instance, the sum of splittable multi-component staple fibers and split staple fibers may comprise at most about any of the following: 75%, 65%, 55%, 50%, 45%, 40%, 35%, and 30% by weight of a total amount of fibers forming the fabric and/or at least about any of the following: 10%, 15%, 20%, 25%, 30%, and 35% by weight of a total amount of fibers forming the fabric.

The fibers forming fabrics, in accordance of certain embodiments of the invention, may comprise substantially 100% or 100% staple fibers. For example, the fabrics may be formed from substantially 100% or 100% staple fibers comprising mono-component staple fibers, split staple fibers, and/or multi-component staple fibers. In accordance with certain embodiments of the invention, the split staple fibers comprise a decitex less than that of the mono-component staple fibers.

In accordance with certain embodiments of the invention, the first group of split staple fibers, the second group of split staple fibers, or both may comprise a non-round cross-section. For example, the non-round cross-section may comprise a pie-shaped cross-section or a ribbon-shaped cross-section. As noted above, the first group of split staple fibers and the second group of split staple fibers may be present due to the complete or partial splitting or separation of individual segments from splittable multi-component staple fibers, in which the "split fiber" may comprise the portion of an individual segment of the splittable multi-component staple fiber that has been separated or split from the original splittable multi-component staple fiber. In this regard, the splittable multi-component staple fibers forming the split staple fibers may be round, multi-lobal, oval, rectangular, etc. The different polymer segments can have many different shapes. For instance, the different polymer segments my comprise, as illustrated in FIGS. 1A-1H, a half-half configuration, crescent configuration, banded configuration, pie configuration, star configuration, petal configuration, etc. In accordance with certain embodiments of the invention, the segments may be formed continuously along the total length of the filaments. The multi-component staple fibers can be split by a number of different methods, such as heat-treatment by hot air, water or steam, as chemical disintegration of the boundary surface by chemical leaching or plasma treatment, as mechanical stressing by physical drawing or bending, by water jet impingement (i.e., hydroentangling). In accordance with certain embodiments of the invention, the splitting of a multi-component staple fiber may normally proceed stepwise, with one internal surface between the segments breaking up at a time. That is, if the splittable fiber includes more than two segments many variants of partly split fibers may coexist in the fabric.

In accordance with certain embodiments of the invention, the mono-component staple fibers comprise a synthetic polymeric material. For example, the synthetic polymeric material comprises at least one of a polyolefin, a polyester, a polyamide, or any combination thereof. In accordance with certain embodiments of the invention, the first polymeric material comprises at least one of a polyolefin, a polyester, a polyamide, or any combination thereof. The second polymeric material, in accordance with certain embodiments of the invention, comprises at least one of a polyolefin, a polyester, a polyamide, or any combination thereof. In accordance with certain embodiments of the invention, the mono-component staple fibers comprise a first polyester, the first polymeric material comprises a second polyester which may be the same or different than the first polyester, and the second polymeric material comprises a polyolefin, such as polypropylene.

In accordance with certain embodiments of the invention, the fabric comprises one or more binders, such as a non-ionic binder. In accordance with certain embodiments of the invention, the bonder comprises an acrylic binder (e.g., a non-ionic acrylic binder). Additionally or alternatively, the binder may comprise a blend of (i) a polyvinyl acetate and acrylic copolymer, and (ii) a non-ionic acrylic binder. In accordance with certain embodiments of the invention, a ratio, based on weight, between the (i) polyvinyl acetate and acrylic copolymer and (ii) the non-ionic acrylic binder ranges from about 6.75:1 to about 3.25:1, such as about 4.5:1. In accordance with certain embodiments of the invention, the ratio, based on weight, between the (i) polyvinyl acetate and acrylic copolymer and (ii) the non-ionic acrylic binder may comprises at most about any of the following: 7:1, 6.75:1, 6.5:1, 6:1, 5.5:1, 5:1, and 4.75:1 and/or at least about any of the following: 2.5:1, 3:1, 3.5:1, 4:1, 4.25:1, 4.5:1, and 4.75:1.

In accordance with certain embodiments of the invention, the binder may further comprises a melamine-formaldehyde copolymer resin. For example, the melamine-formaldehyde copolymer resin may comprise a methylated or partially methylated melamine-formaldehyde copolymer resin. In accordance with certain embodiments of the invention, a ratio between (i) the non-ionic acrylic binder and (ii) the melamine-formaldehyde copolymer resin comprises, based on weight, from about 1:1 to about 2:1, such as about 1.3:1. In accordance with certain embodiments of the invention, the ratio, based on weight, between the (i) the non-ionic acrylic binder and (ii) the melamine-formaldehyde copolymer resin may comprises at most about any of the following: 2.5:1, 2.25:1, 2:1, 1.75:1, 1.5:1, and 1.25:1 and/or at least about any of the following: 0.75:1, 1:1, 1.1:1, 1.2:1, and 1.25:1.

In accordance with certain embodiments of the invention, the fabric may further comprise a surfactant, which may in incorporated separately or within the binder (e.g., a binder system including one or more binder components and one or more surfactants). The surfactant, in accordance with certain embodiments of the invention, my comprise anionic, cat-ionic, and/or amphoteric surfactants. In accordance with certain embodiments of the invention, the surfactant may comprise a betaine, a lauramine (e.g., lauramine oxide, sodium laurimino dipropionate, etc.), a siloxane, a stearate, or combinations thereof. In accordance with certain embodiments of the invention, the surfactant may comprise an amphoteric surfactant described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. In accordance with certain embodiments of the invention, the surfactant may comprise Cirrasol™ PE1185, which is commercially available from Croda.

In accordance with certain embodiments of the invention, a ratio between (i) the surfactant and (ii) the non-ionic acrylic binder may comprise, based on weight, from about 1:1 to about 2.5:1, such as about 1.2:1. In accordance with certain embodiments of the invention, the ratio, based on weight, between the (i) the surfactant and (ii) the non-ionic acrylic binder may comprises at most about any of the following: 2.5:1, 2.25:1, 2:1, 1.75:1, 1.5:1, and 1.25:1 and/or at least about any of the following: 0.75:1, 1:1, 1.1:1, 1.2:1, and 1.25:1.

In accordance with certain embodiments of the invention, the fabric may comprises a dry-wipe, which may be suitable for impregnation with a disinfectant solution for subsequent application onto a surface to be cleaned. In accordance with certain embodiments of the invention, the fabric maintains a substantially constant disinfectant concentration in a disinfectant solution when the fabric is disposed therein. For example, the disinfectant concentration in the disinfectant solution has less than a 10% reduction over a four hour time period when the fabric is disposed or submerged therein. The disinfectant may comprise a quaternary ammonium compound or chlorine-based disinfectant. In accordance with certain embodiments of the invention, the disinfectant concentration in the disinfectant solution has less than a 15% reduction over a twenty-four hour time period when the disinfectant comprises a quaternary ammonium compound. In accordance with certain embodiments of the invention, the disinfectant concentration in the disinfectant solution has less than a 20% reduction over a four hour time period when the disinfectant comprises chlorine.

In accordance with certain embodiments of the invention, the fabric may comprise a Martindale Abrasion value of less than about 6 mg as determined by IST 20.5, such as less than about 5 mg, less than about 4 mg, less than about 3 mg, less than about 2 mg, less than about 1.75 mg, or less than about 1.50 mg as determined by IST 20.5. In accordance with certain embodiments of the invention, for instance, the fabric may comprise a Martindale Abrasion value of at most about any of the following: 6, 5, 4, 3, 2, 1.75, and 1.5 mg as determined by IST 20.5 and/or at least about any of the following: 0.25, 0.50, 0.75, 1.0, 1.25, and 1.5 mg as determined by IST 20.5.

The fabric, in accordance with certain embodiments of the invention, may comprise a first table dwell time of about 14 minutes or less, such as about 13 minutes or less, or about 12 minutes or less. In accordance with certain embodiments of the invention, for instance, the fabric may comprise a first table dwell time of at most about any of the following: 14, 13, 12, 11, 10, and 9 minutes and/or at least about any of the following: 9, 9.50, 10, 10.5, 11, and 12 minutes.

The fabric, in accordance with certain embodiments of the invention, may comprise an initial nominal dwell time of about 0.25 min/gsm or less, such as about 0.23 min/gsm or less, or about 0.21 min/gsm or less, or about 0.20 min/gsm or less, or about 0.19 min/gsm or less, or about 1.8 min/gsm or less, or about 1.6 min/gsm or less; wherein the initial nominal dwell time is the first table dwell time divided by the dry weight of the fabric. The fabric, in accordance with certain embodiments of the invention, may comprise an absorption capacity of about 700% or more as determined by IST 010.1, such as about 800% or more, or about 900% or more, or about 1000% or more, or about 1100% or more, or about 1200% or more as determined by IST 010.1.

In another aspect, the present invention provides a fabric comprising a blend of physically entangled fibers. In accordance with certain embodiments of the invention, the blend of fibers may comprise mono-component staple fibers comprising from about 1 to about 4 decitex (dtex) and splittable multi-component staple fibers comprising from about 1 to about 4 dtex, in which the splittable multi-component staple fibers include at least about 6 splittable segments and the splittable multi-component staple fibers comprise from about 15 to about 50% by weight of the blend of fibers. In accordance with certain embodiments of the invention, the mono-component staple fibers and splittable multi-component staple fibers define a carded web, which may optionally be devoid of synthetic and/or natural cellulosic material. In accordance with certain embodiments of the invention, the fabric may comprise a combination of mono-component staple fibers, one of more groups of split staple fibers, and/or spittable multi-component staple fibers.

In accordance with certain embodiments of the invention, the splittable multi-component staple fibers may include from about 6 to about 20 splittable segments. In accordance with certain embodiments of the invention, for instance, the splittable multi-component staple fibers may include at most about any of the following: 20, 18, 16, 14, 12, 10, 8 and 6 splittable segments and/or at least about any of the following: 2, 4, 6, 8, 10, and 12 splittable segments.

In accordance with certain embodiments of the invention, the splittable multi-component staple fibers, which can be used to form split staple fibers, may be round or non-round cross-section (e.g., multi-lobal, oval, rectangular, etc.). The different polymer segments can have many different shapes. For instance, the different polymer segments my comprise, as illustrated in FIGS. 1A-1H, a half-half configuration, crescent configuration, banded configuration, pie configuration, star configuration, petal configuration, etc. In accordance with certain embodiments of the invention, the segments may be formed continuously along the total length of the filaments. The multi-component staple fibers can be split by a number of different methods, such as heat-treatment by hot air, water or steam, as chemical disintegration of the boundary surface by chemical leaching or plasma treatment, as mechanical stressing by physical drawing or bending, by water jet impingement (i.e., hydroentangling). In accordance with certain embodiments of the invention, the splitting of a multi-component staple fiber may normally proceed stepwise, with one internal surface between the segments breaking up at a time. That is, if the splittable fiber includes more than two segments many variants of partly split fibers may coexist in the fabric.

In accordance with certain embodiments of the invention, the splittable segments may comprise at least a first component comprising a first polymeric material and a second component comprising a second polymeric material that is different than the first polymeric material. The mono-component staple fibers, in accordance with certain embodiments of the invention, may comprise a synthetic polymeric material. The synthetic polymeric material, for example, may comprises at least one of a polyolefin, a polyester, a polyamide, or any combination thereof. The first polymeric material and the second polymeric material, for example, may independently comprise at least one of a polyolefin, a polyester, a polyamide, or any combination thereof.

In accordance with certain embodiments of the invention, the mono-component staple fibers comprise a first polyester, the first polymeric material comprises a second polyester which may be the same or different than the first polyester, and the second polymeric material comprises a polyolefin, such as polypropylene. The splittable multi-component fibers, in accordance with certain embodiments of the invention, may comprise splittable bi-component fibers comprising from about 6 to about 20 splittable segments, as noted above, in which about a first half of the splittable segments comprise the first polymeric material and a second half of the splittable segments comprise the second polymeric material.

In accordance with certain embodiments of the invention, the splittable multi-component staple fibers may have a linear mass density of at most about 5 decitex (dtex), such as at most about 4, 3, 2.5, 2, or 1.5 dtex. In accordance with certain embodiments of the invention, for example, the splittable multi-component staple fibers may have a linear mass density of at most about any of the following: 6, 5.5, 5, 4.5, 4, 3.5, 3, 2.5, 2, and 1.5 dtex and/or at least about any of the following: 1, 1.25, 1.5, 1.75, and 2.0 dtex.

In accordance with certain embodiments of the invention, the splittable segments may independently have a linear mass density of at most about 1 decitex (dtex), such as at most about 0.75, 0.5, 0.25, 0.2, 0.1, 0.75, or 0.5 dtex. In accordance with certain embodiments of the invention, for example, the splittable segments may independently comprise at most about any of the following: 1, 0.75, 0.5, 0.25, 0.2, 0.1, 0.75, 0.5, and 0.25 dtex and/or at least about any of the following: 0.05, 0.075, 0.1, 0.125, 0.15, 0.2, and 0.25 dtex.

In another aspect, the present invention provides a method for forming a fabric, such as a fabric disclosed herein. In accordance with certain embodiments of the invention, the method comprises providing a blend of fibers, in which the blend of fibers comprises (a) mono-component staple fibers comprising from about 1 to about 4 decitex (dtex) and (b) splittable multi-component staple fibers comprising from about 1 to about 4 dtex. The splittable multi-component staple fibers, for example, may include at least about 6 splittable segments and the splittable multi-component staple fibers may comprise from about 15 to about 50% by weight of the blend of fibers. The method may further comprise physically entangling the blend of fibers to at least partially split the splittable multi-component staple fibers and to provide a consolidated nonwoven. In accordance with certain embodiments of the invention, the step of physically entangling the blend of fibers comprises hydroentangling the blend of fibers. In accordance with certain embodiments of the invention, the method may further comprise blending and carding the mono-component staple fibers and the splittable multi-component staple fibers prior to the physically entangling step (e.g., hydroentangling). In accordance with certain embodiments of the invention, the method may further comprise applying a binder and/or surfactant to the fabric, such as after the physically entangling step (e.g., hydroentangling).

In yet another aspect, the present invention provides a method of treating a surface (e.g., disinfecting a surface). In accordance with certain embodiments of the invention, the method may comprise a step of providing a fabric (e.g., a wipe) according to a fabric disclosed herein and applying a liquid disinfectant composition to the fabric. The method may further comprise contacting the surface with the fabric to transfer at least a portion of the liquid disinfectant onto the surface. In accordance with certain embodiments of the invention, the step of applying a liquid disinfectant composition to the fabric comprises submerging the fabric into a container holding the liquid disinfectant.

EXAMPLES

The present disclosure is further illustrated by the following examples, which in no way should be construed as being limiting. That is, the specific features described in the following examples are merely illustrative and not limiting.

Test Methods

Basis weight was measured as per the Standard test ASTM D3776.

The thickness of the samples was measured as per the standard test ASTM D5729.

For evaluating abrasion resistance the Martindale Abrasion Test method used was IST 020.5 modified with a plastic abradant and was run wet for 96 cycles. The sample was dried and the fuzz shaved off. The differences in the weights of the samples before and after Martindale step in milligrams were recorded. A lower value indicates better abrasion resistance.

Wet Crock resistance was measured as per the standard test AATCC TM8.

The absorption time and capacity were measured as per IST 010.1. The units for the absorption time is recorded in seconds and the capacity is reported in %, based on weight of liquid absorbed by weight of the sample.

Wet grab tensile strength and elongation were measured as per the standard test method ASTM D5034.

Dwell Time was determined by a method in which 4 cafeteria style tables having a melamine laminate smooth and non-absorbing type surface were used for analysis. Each table had a surface of 1369 square inches (0.8832 sq.m.). A wipe of size of 11.5"×13" is removed from a bucket containing the Quat disinfecting solution at a concentration of 220 ppm and the excess liquid is squeezed out using a mechanical roller used for towels in order to avoid dripping during transportation from the bucket to the table. Then the four tables were wiped with the same wipe and a timer was started for each table as an operator finishes wiping it. The times reported for each table is the elapsed time for that surface to dry completely. For a good comparison, the operator has to be the same for all the samples being compared to avoid gross variability on how the wipe was squeezed out. For each example, this procedure was repeated three times for the Quat disinfecting solution and the average was reported. The process was also repeated for the chlorine disinfectant.

The dwell time ratio 1 is the ratio for the drying time for table 1 and table 4.

The initial nominal dwell time is the dwell time for the first table divided by the dry weight of the wipe. For this test, the room should was kept between 68 and 77° F. and the relative humidity was kept between 40 and 60%.

Depletion of quat solution by the wipe was evaluated as follows. One gallon of a Quat solution at a concentration of 220 mg/l or 220 ppm was placed in bucket #1, #2 and #3. A half-gallon of the same solution was placed in bucket #4. For a given example being tested, a wipe having dimensions of 12"×12" was added to each of buckets #1, #2, and #3. Each of these buckets was loosely covered to avoid atmospheric contamination. After 24 hours, a sample of the disinfecting solution was taken from each of the 4 buckets and titrated for Quat content. The ratio of the concentrations of bucket #4 "Cqs" with respective concentration in the three other buckets "Cqw" was used to calculate the % retention of disinfectant. The average result was reported as follows: % Retained=100*Cqw/Cqs.

Depletion of chlorine solution by the wipe was determined as follows. One gallon of chlorine solution at a concentration of 110 mg/l or 110 ppm was placed in bucket #1, #2 and #3. A half-gallon gallon of the same solution was placed into bucket #4. For a given example being tested, a wipe having dimensions of 12"×12" was added to each of buckets #1, #2, and #3. Each of these buckets were loosely covered to avoid atmospheric contamination. After 4 hours, a sample of the disinfecting solution was taken from each of the 4 buckets and titrated for chlorine content. The ratio of the concentrations of bucket #4 "Ccs" with respective concentration in the three other buckets "Ccw" was used to calculate the % retention of disinfectant. The average result was reported as follows: % Retained=100*Ccw/Ccs.

Example 1

Example 1 consisted of a 61 gsm hydroentangled carded web that was free of cellulosic fibers. Two polyester fibers accounted for 95% by weight of the final sample, binders accounted for 3.25% by weight of the final sample, and residual moisture accounted for 1.75% of the final sample. The nonwoven was made by opening, blending, and carding a 1:1 blend of the two fibers. The first fiber was a 1.8 dtex polyester staple fiber having a 38 mm length and a standard hydrophilic spin finish. The second fiber was a 1.7 dtex polyester staple fiber having a 38 mm length and a durable hydrophilic finish. This web was hydroentangled and imaged on an imaging drum to provide a hydoentangled nonwoven fabric. Subsequently, the hydoentangled nonwoven fabric was saturation coated with a binder solution. The binder application step was followed by a drying step and curing the binder using banks of steam cans prior to winding and slitting. The binder solution contained on a dry basis about 78% of a polyvinyl acetate and acrylic copolymer binder, 13% of a melamine-formaldehyde copolymer extender resin, 6% of a surfactant, and the remaining 3% consisting of pigments, antifoam, and ammonium chloride.

Figure 2:
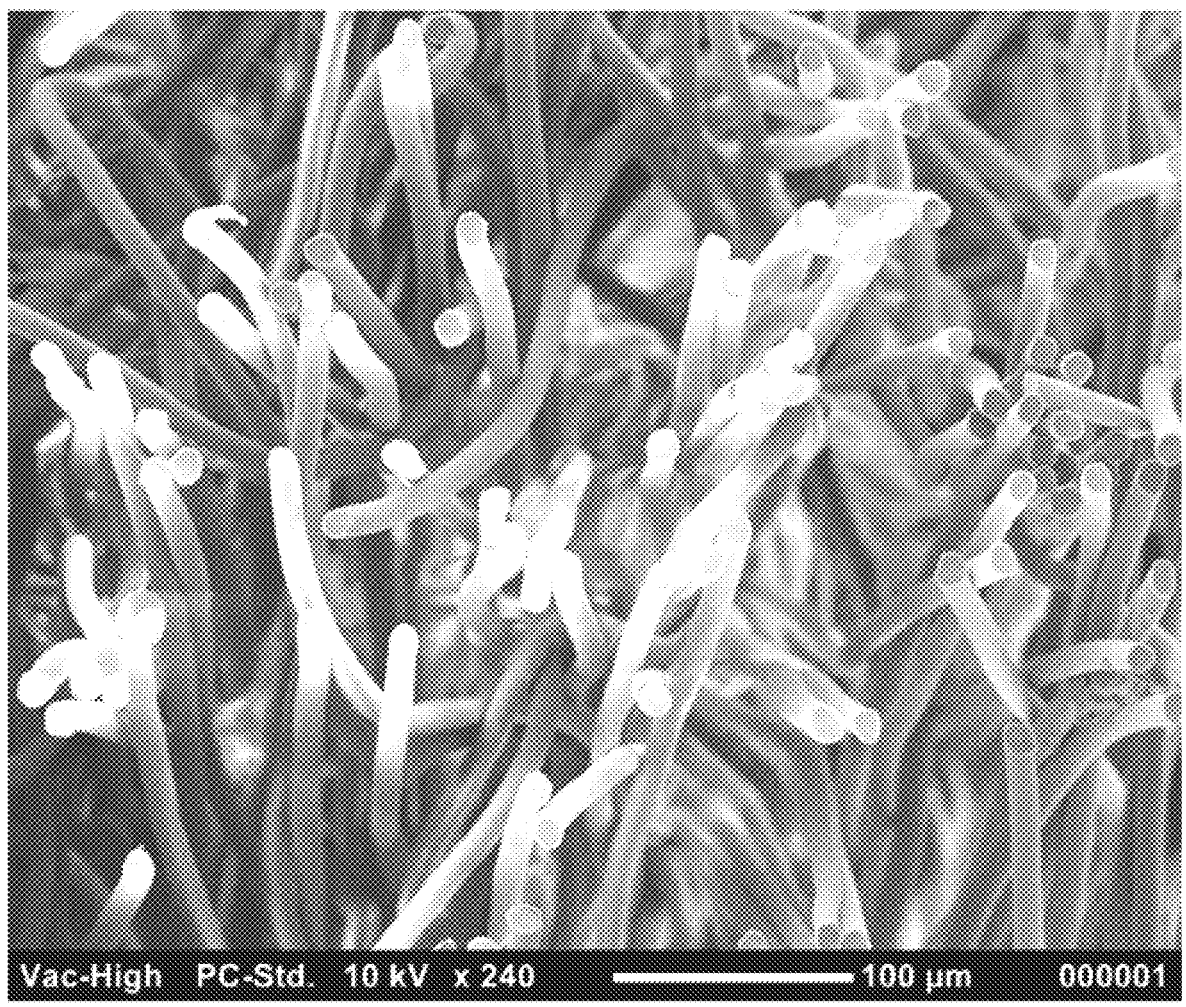
FIG. 2 illustrates a cross-section view for the fabric from Example 1.

This sample exhibited very good abrasion resistance and lack of reactivity with either of the sanitizers. However, this sample had large pores resulting in poor initial dwell time as the solution gets squeezed out of the wipe easily upon the onset of use. FIG. 2 illustrates a cross-section view for the fabric from Example 1.

Example 2

This sample consisted of a 61 gsm hydroentangled carded web that was free of cellulosic fibers. This web was made from 71% by weight of polyester fibers, 24% by weight of bicomponent splittable fibers, 4% by weight of binders, and about 1% by weight of residual moisture. The nonwoven is made by opening, blending, and carding a blend made from (i) 1.8 dtex polyester staple fibers having a 38 mm length and having a standard hydrophilic spin finish and (ii) 2.2 decitex splittable pie-type bicomponent fibers that was 51 mm long and had 16 segments, in which the these segments include segments formed from nylon (PA) and segments formed from polyester (PET), and having a typical spin finish. This web was hydroentangled and subsequently saturation coated with a binder solution. This binder application step was followed by drying the web and curing the binder using banks of steam cans prior to winding and slitting. The binder solution contained on a dry basis about 73% of a vinyl acetate and ethylene copolymer binder, about 10% of a melamine-formaldehyde copolymer extender resin, 15% of a polyester ether wetting agent, and the remaining 2% consisting of pigments, antifoam, and ammonium chloride.

This example illustrates the benefit of the microfiber (e.g., the split fibers formed during the hydroentangling step) on the dwell time. The hydroentangled fabric has a tighter pore size that exhibits a greater ability to retain the solution and allow a more controlled release of the disinfectant. However, the microfibers created by the splitting of the bicomponent fibers are easily abraded as shown by the increase in Martindale abrasion results. Finally, this sample has not performed well in regard to depletion of the chlorine disinfectant due to the binder system used. For instance, the titration results for the fiber alone suggest that the PA/PET fibers were substantially inert and not binding the disinfectant. As such, this particular binder system appears to be somewhat reactive with the chlorine disinfectant (e.g., depletes the chlorine concentration). Moreover, this sample did not perform as well as sample 1 in a subjective stain resistance test.

Example 3

This sample consisted of a 61 gsm hydroentangled carded web that is free of cellulosic fibers. This web was made from 71% by weight of polyester fibers, 24% by weight of bicomponent splittable fibers, 4% by weight of binders, and about 1% by weight of residual moisture. The nonwoven is made by opening, blending, and carding a blend made from (i) 1.8 dtex polyester staple fibers having a 38 mm length and having a standard hydrophilic spin finish and (ii) 2.2 dtex splittable pie-type bicomponent fibers that was 51 mm long and had 16 segments, in which these segments include segments formed from nylon (PA) and segments formed from polyester (PET), and having a typical spin finish. This web was hydroentangled and subsequently saturation coated with a binder solution. This binder application step was followed by drying the web and curing the binder using banks of steam cans prior to winding and slitting. The binder solution contained on a dry basis about 60% of a vinyl acetate and ethylene copolymer binder, about 10% of a melamine-formaldehyde copolymer extender resin, 15% of a surfactant, 13% acrylic binder known as Acrygen 61192 from Omnova Solutions Inc., and the remaining 2% consisting of pigments, antifoam, and ammonium chloride.

This example illustrates the benefit of the microfiber (e.g., the split fibers formed during the hydroentangling step) on the dwell time. The hydroentangled fabric has a tighter pore size that exhibits a greater ability to retain the solution and allow a more controlled release of the disinfectant. However, the microfibers created by the splitting of the bicomponent fibers are easily abraded as shown by the increase in Martindale abrasion results. Finally, this sample has not performed well in regard to depletion of the chlorine disinfectant due to the binder system used. For instance, the titration results for the fiber alone suggest that the PA/PET fibers were substantially inert and not binding the disinfectant. Moreover, the wipe did not perform as well as sample 1 in a subjective stain resistance test.

Example 4

This sample consisted of a 56 gsm hydroentangled carded web that is free of cellulosic fibers. This web is made from about 71% by weight polyester fibers, 24% by weight of bicomponent splittable fibers, 3.5% by weight of binders, and about 1.5% by weight of residual moisture. The nonwoven is made by opening, blending, and carding a blend made from (i) 1.8 dtex polyester staple fibers having a 38 mm length and having a standard hydrophilic spin finish and (ii) 2.2 dtex splittable pie type bicomponent fibers having a length of 51 mm and being made of 16 segments, in which these segments include segments formed from polypropylene (PP) and segments formed from polyester (PET) and having a typical spin finish. This web was hydroentangled and subsequently saturation coated with a binder solution. This step was followed by drying the web and curing the binder using banks of steam cans prior to winding and slitting. The binder solution contained on a dry basis about 68% of a polyvinyl acetate and acrylic copolymer binder, about 11.5% of a melamine-formaldehyde copolymer extender resin, 18.5% of a polyester ether wetting agent, and the remaining 2% consisted of pigments, antifoam, and ammonium chloride.

This example illustrates the impact of the microfiber (e.g., the split fibers formed during the hydroentangling step) on the dwell time as well as the impact of binder selection on having a wipe that is not reactive with the Quat and chlorine disinfectants. These benefits were realized even when the type of splittable fiber used was different (PP/PET vs. PA/PET). However, this sample still suffers from poor abrasion resistance. This wipe performed as well as Example 1 in a subjective stain resistance test.

Example 5

This sample consisted of a 68 gsm hydroentangled carded web that was free of cellulosic fibers. This web was made from about 80% by weight polyester fibers, 14% by weight of bicomponent splittable fibers, 4.5% by weight of binders, and about 1.5% by weight of residual moisture. The nonwoven was made by opening, blending, and carding a blend made from (i) a 1.8 dtex polyester staple fiber having a 38 mm length having a standard hydrophilic spin finish and (ii) a 2.2 dtex splittable pie type bicomponent fibers having a length of 51 mm and being made of 16 segments, in which these segments include segments formed from polypropylene (PP) and segments formed from polyester (PET) and having a typical spin finish. This web was hydroentangled and subsequently saturation coated with a binder solution. This step was followed by drying the web and curing the binder using banks of steam cans prior to winding and slitting. The binder solution contained on a dry basis about 59% of a polyvinyl acetate and acrylic copolymer binder, 13% of an acrylic binder known as Acrygen 61192 from Omnova Solutions Inc., about 10% of a melamine-formaldehyde copolymer extender resin, 16% of a polyester ether wetting agent, and the remaining 2% consisting of pigments, antifoam, and ammonium chloride.

This example illustrates increased abrasion resistance of the microfibers. However, this sample had poor dwell time. This poor dwell time performance as well as the lower absorption capacity suggests an incompatibility of the binder and the surfactant.

Example 6

This example consisted of a 63 gsm hydroentangled carded web that was free of cellulosic fibers. This web was made from about 80% by weight polyester fibers, 14% by weight of bicomponent splittable fibers, 4.5% by weight binders, and about 1.5% by weight of residual moisture. The nonwoven was made by opening, blending, and carding a blend made from (i) 1.8 dtex polyester staple fibers having a 38 mm length and having a standard hydrophilic spin finish and (ii) 2.2 dtex splittable pie type bicomponent fibers having a length of 51 mm and being made of 16 segments; in which these segments include segments formed from polypropylene (PP) and segments formed from polyester (PET) and having a typical spin finish. This web was hydroentangled and subsequently saturation coated with a binder solution. This step was followed by drying the web and curing the binder using banks of steam cans prior to winding and slitting. The binder solution contained on a dry basis about 59% of a polyvinyl acetate and acrylic copolymer binder, 13% of an acrylic binder known as Acrygen 61192 from Omnova Solutions Inc., about 10% of a melamine-formaldehyde copolymer extender resin, 16% of a Cirrasol PE1185 surfactant from Croda, and the remaining 2% comprising of pigments, antifoam, and ammonium chloride.

Figure 3:
FIG. 3 illustrates a cross-section view for the fabric from Example 6.

In this example, the use of microfibers created by splitting of bicomponent fibers with the use of the secondary acrylic binder (e.g., a non-ionic acrylic binder known as Acrygen 61192 from Omnova Solutions Inc.) that improves the abrasion resistance of those microfibers. Additionally, the surfactant was compatible and created adequate wettability of the sample. With this combination, the sample realized good dwell time performance, good absorbency, non-reactivity with both sanitizers, and good abrasion resistance. This sample performed as well as example 1 in regards to resistance to stain. FIG. 3 illustrates a cross-section view of the fabric from Example 6.

The results for Examples 1-6 are summarized in Tables 1 and 2.

TABLE 1

| Test name | Units | Ex 1 | Ex 2 | Ex 3 | Ex 4 | Ex 5 | Ex 6 |
| --- | --- | --- | --- | --- | --- | --- | --- |
| Basis weight | g/m2 | 61 | 68 | 64 | 56 | 68 | 63 |
| Thickness | Mm | 28 | 24 | 24.5 | 24 | 29 | 31 |
| Martindale abrasion | Mg | 1.11 | 3.4 | 3 | 11.6 | 3 | 1.73 |
| Wet Crock rating | | >3.5 | 4.5 | 4.5 | 3.5 | 3 | 4.5 |
| Absorption time | Second | 2 | 10.7 | 5.1 | 97 | No sink | 34 |
| Absorption capacity | % | 1080 | 819 | 849 | 1027 | 488 | 1070 |
| Wet Grab tensile strength - MD/CD | Lbs | 40/20 | 42/25 | 37/23 | 29/24 | 27/20 | 46/29 |
| Wet Grab Elongation - MD/CD | % | 45/135 | 43/67 | 39/65 | 44/73 | 59/97 | 39/83 |
| Dwell time - table 1 | Minutes | 16:54 | 13:31 | 13:37 | 8:32 | 22:04 | 11:59 |
| Dwell time - table 2 | Minutes | 8:53 | 7:39 | 7:45 | 4:55 | 11:46 | 5:12 |
| Dwell time - table 3 | Minutes | 6:06 | 6:02 | 5:52 | 5:07 | 7:05 | 4:03 |
| Dwell time - table 4 | Minutes | 3:49 | 5:12 | 4:04 | 3:04 | 5:34 | 3:06 |
| Dwell time ratio 1 | Dwell time 1:Dwell time 4 | 4.7 | 2.6 | 3.3 | 2.4 | 4.2 | 3.7 |
| Initial nominal dwell time | Minutes/gsm | 0.27 | 0.196 | 0.209 | 0.148 | 0.324 | 0.184 |
| Quat titration @ 24 hours - % of concentration retained | % | 96 | 88 | 91 | 93 | 90 | 96 |
| Chlorine titration @ 4 hours - % | % | 83 | 83 | 83 | 86 | 81 | 93 |

TABLE 2

| Fiber type | Titration for Quat - 4 Hours % of 220 ppm Quat solution retained | Titration for chlorine - 4 hours % of 110 ppm chlorine solution of chlorine retained |
|---|---|---|
| 1.8 Dtex PET fibers | 94 | 98 |
| 1.7 Dtex PET permanent hydrophilic finish | 100 | 100 |
| PA/PET 2.2 Dtex splittable fiber | 91 | 87 |
| PP/PET 2.2 Dtex splittable fiber | 92 | 97 |
| Rayon | 47 | 87 |

A comparison of Example 1 to Examples 3, 4, and 6 illustrate the value of using splittable fibers as a way to manage the dwell time. Example 5 did not support this trend. However, we attribute this poor performance to the mismatch between the secondary binder system and the surfactant used; that mismatch reduced the overall wettability of the sample. A comparison of Examples 2, 3, 4, 5, and 6 illustrate the benefit of using the secondary acrylic based binder on the control of abrasion for the microfibers (e.g., split fibers).

These and other modifications and variations to the invention may be practiced by those of ordinary skill in the art without departing from the spirit and scope of the invention, which is more particularly set forth in the appended claims. In addition, it should be understood that aspects of the various embodiments may be interchanged in whole or in part. Furthermore, those of ordinary skill in the art will appreciate that the foregoing description is by way of example only, and it is not intended to limit the invention as further described in such appended claims. Therefore, the spirit and scope of the appended claims should not be limited to the exemplary description of the versions contained herein.

That which is claimed:

1. A fabric, comprising:
   (i) mono-component staple fibers comprising from about 1 to about 4 decitex (dtex);
   (ii) a first group of split staple fibers comprising from about 0.05 to about 0.5 dtex, wherein the first group of split fibers comprise a first polymeric material;
   (iii) a second group of split staple fibers comprising from about 0.05 to about 0.5 dtex, wherein the second group of split fibers comprise a second polymeric material that is different than the first polymeric material; and
   (iv) a binder comprising a non-ionic acrylic binder and a melamine-formaldehyde copolymer resin, wherein the melamine-formaldehyde copolymer resin comprises a methylated or partially methylated melamine-formaldehyde copolymer resin, and wherein the binder includes a first ratio between (i) the non-ionic acrylic binder and (ii) the melamine-formaldehyde copolymer resin comprises from about 0.75:1 to about 2.5:1;
   wherein the mono-component staple fibers, the first group of split staple fibers, and the second group of split staple fibers are physically entangled together to define a consolidated nonwoven being devoid of synthetic and natural cellulosic material, and wherein a total amount of split fibers comprises from about 10% to 40% by weight of a total amount of fibers forming the fabric, wherein the total amount of split fibers is defined by the sum of the first group of split staple fibers and the second group of split staple fibers.

2. The fabric of claim 1, wherein the consolidated nonwoven comprises a hydroentangled nonwoven.

3. The fabric of claim 1, wherein the total amount of split fibers comprises from about 10% to 30% by weight of the total amount of fibers forming the fabric.

4. The fabric of claim 1, wherein the first group of split staple fibers, the second group of split staple fibers, or both comprise a non-round cross-section.

5. The fabric of claim 1, wherein the mono-component staple fibers comprise a synthetic polymeric material comprising at least one of a polyolefin, a polyester, a polyamide, or any combination thereof.

6. The fabric of claim 1, wherein the first polymeric material comprises at least one of a polyolefin, a polyester, a polyamide, or any combination thereof, and the second polymeric material also comprises at least one of a polyolefin, a polyester, a polyamide, or any combination thereof.

7. The fabric of claim 1, wherein the mono-component staple fibers comprise a first polyester, the first polymeric material comprises a second polyester that is the same or different than the first polyester, and the second polymeric material comprises a polyolefin.

8. The fabric of claim 1, wherein the binder further comprises a polyvinyl acetate and acrylic copolymer.

9. The fabric of claim 8, further comprising a second ratio between the (i) polyvinyl acetate and acrylic copolymer and (ii) the non-ionic acrylic binder from about 6.75:1 to about 3.25:1.

10. The fabric of claim 1, wherein the ratio between (i) the non-ionic acrylic binder and (ii) the melamine-formaldehyde copolymer resin comprises from about 1:1 to about 2:1.

* * * * *